(12) United States Patent
White et al.

(10) Patent No.: US 7,713,709 B2
(45) Date of Patent: May 11, 2010

(54) ASSAY FOR DETECTION OF ANTIBODIES TO LYSOSOMAL ENZYMES

(75) Inventors: Joleen White, San Francisco, CA (US); Lisa Argento Flay, Mill Valley, CA (US); Erik Foehr, Novato, CA (US); Gary Taniguchi, San Francisco, CA (US); William S. Prince, San Rafael, CA (US); Bin Zhao, San Ramon, CA (US)

(73) Assignee: Biomarin Pharmaceutical Inc., Novato, CA (US)

( * ) Notice: Subject to any disclaimer, the term of this patent is extended or adjusted under 35 U.S.C. 154(b) by 492 days.

(21) Appl. No.: 11/724,983

(22) Filed: Mar. 16, 2007

(65) Prior Publication Data

US 2008/0003626 A1    Jan. 3, 2008

Related U.S. Application Data

(60) Provisional application No. 60/783,690, filed on Mar. 17, 2006.

(51) Int. Cl.
*G01N 33/53*   (2006.01)

(52) U.S. Cl. .................. 435/7.1; 435/7.21; 436/501; 436/518; 424/9.1

(58) Field of Classification Search ........................ None
See application file for complete search history.

(56) References Cited

U.S. PATENT DOCUMENTS 4,391,904 A   7/1983   Litman et al.

2005/0287133 A1   12/2005   Qin et al.

FOREIGN PATENT DOCUMENTS

WO   WO-01/69260   9/2001

OTHER PUBLICATIONS

"Current Protocols in Immunology," Unit 6.11 (2006).
Ao et al., *Anal. Chem.*, 78:1104-1106 (2006).
Cui et al., *J. Phys. Chem. B*, 110(9):4002-4006 (2006).
Dai et al., *Cancer Detect. Prev.*, 29:233-240 (2005).
Dintzis et al., *J. Biol. Chem.*, 269:12159-12166 (1994).
Ghindilis, *Biochem. Soc. Trans.*, 28:84-89 (2000).
Kakkis, *Expert Opin. Investig. Drugs*, 11(5):675-685 (2002).
Klock et al., *Internat. Pediatr.*, 9:40-48 (1994).
Liu et al., *J. Immunol. Methods*, 307:34-40 (2005).
Linthorst et al., *Kidney International*, 66(4):1589-1595 (2004).
Marnelll et al., *J. Cell. Biol.*, 99(6):1907-1916 (1984).
Mire-Sluis et al., *J. Immunological Methods*, 289:1-16 (2004).
Muenzer, *Adv. Pediatri.*, 33:269-302 (1986).
Munier-Lehmann et al., *Bichom. Soc. Trans.*, 2491:133-136 (1996).
Neufeld et al., "The Mucopolysaccaridoses," *The Metabolic Basis of Inherited Disease*, New York, pp. 1565-1587 (1989).
Schultz et al., *Proc. Natl. Acad. Sci. USA*, 97:996-1001 (2000).
Starr et al., *Glycosylation & Disease*, 1:165-176 (1994).
Sun et al., *Analytical Letters*, 34:1627-1637 (2001).
Tang et al., *Biosens. Bioelectron.* (2005).
Valenzano et al., *Analytical Biochemistry*, 209:156-162 (1993).
International Search Report for International Application No. PCT/US2007/006677, dated Nov. 8, 2007.

*Primary Examiner*—Lisa V Cook
(74) *Attorney, Agent, or Firm*—Marshall, Gerstein & Borun LLP

(57)   ABSTRACT

The present invention relates to methods for screening body fluids or tissues for antibodies, including neutralizing and isotype-specific antibodies, against lysosomal enzymes administered as part of enzyme replacement therapy.

16 Claims, No Drawings

ASSAY FOR DETECTION OF ANTIBODIES TO LYSOSOMAL ENZYMES

CROSS-REFERENCE TO RELATED APPLICATIONS

This application claims the benefit of U.S. Provisional Patent Application No. 60/783,690 filed on Mar. 17, 2006, the disclosure of which is herein incorporated by reference in its entirety.

FIELD OF THE INVENTION

The present invention relates to methods for screening body fluids or tissues for antibodies, including neutralizing and isotype-specific antibodies, against lysosomal enzymes administered as part of enzyme replacement therapy.

BACKGROUND OF THE INVENTION

Lysosomal storage diseases known as mucopolysaccharidoses (MPS) (Klock et al., *Internat Pediatr.* 9:40-48 (1994); Starr et al., *Glycosylation & Disease* 1:165-176 (1994)) are caused by a deficiency in an enzyme or combination of enzymes. These lysosomal storage diseases are characterized by intralysosomal accumulation of undegraded glycosaminoglycans, excessive urinary excretion of glycosaminoglycans, progressive mental and physical deterioration, and premature death. Patients are usually born without the visible clinical features of MPS, but develop progressive clinical involvement. Each type of MPS has specific lysosomal enzyme deficiency with a characteristic degree of organ involvement and rate of deterioration. See Muenzer, *Adv. Pediatri.* 33:269-302 (1986).

For example, MPS VI (Maroteaux-Lamy syndrome) is a lysosomal storage disease in which the affected patients lack the enzyme N-acetylgalactosamine-4-sulfatase (ASB). The enzyme metabolizes the sulfate moiety of glycosaminoglycan (GAG) dermatan sulfate (Neufeld et al., "The mucopolysaccharidoses" The Metabolic Basis of Inherited Disease, Eds. Scriver et al., New York:McGraw-Hill, 1989, pp. 1565-1587). In the absence of the enzyme, the stepwise degradation of dermatan sulfate is blocked and the substrate accumulates intracellularly in the lysosome in a wide range of tissues. The accumulation causes a progressive disorder with multiple organ and tissue involvement in which the infant appears normal at birth, but usually dies before puberty. The diagnosis of MPS VI is usually made at 6-24 months of age when children show progressive deceleration of growth, enlarged liver and spleen, skeletal deformities, coarse facial features, upper airway obstruction, and joint deformities. Progressive clouding of the cornea, communicating hydrocephalus, or heart disease may develop in MPS VI children. Death usually results from respiratory infection or cardiac disease. MPS VI is not typically associated with progressive impairment of mental status, although physical limitations may impact learning and development. Although most MPS VI patients have the severe form of the disease which is usually fatal by the teenage years, affected patients with a less severe form of the disease have been described who may survive for decades.

Some patients die from disease-related complications between childhood and early adulthood. One way to treat lysosomal storage diseases is by intravenous enzyme replacement therapy (ERT) (Kakkis, *Expert Opin Investig Drugs* 11(5):675-85 (2002)). ERT takes advantage of the vasculature to carry enzyme from a single site of administration to most tissues. Once the enzyme has been widely distributed, it must be taken up into cells. The basis for uptake into cells is found in a unique feature of lysosomal enzymes: lysosomal enzymes constitute a separate class of glycoproteins defined by phosphate at the 6-position of terminal mannose residues. Mannose 6-phosphate is bound with high affinity and specificity by a receptor found on the surface of most cells (Munier-Lehmann et al., *Biochem. Soc. Trans.* 24(1): 133-6 (1996); Marnell et al., *J. Cell. Biol.* 99(6):1907-16 (1984)). The mannose 6-phosphate receptor (MPR) directs uptake of enzyme from blood to tissue and then mediates intracellular routing to the lysosome.

Recombinant human ASB (rhASB) has been developed as an enzyme replacement therapy for the treatment of MPS VI. RhASB is internalized into the lysosome through the Calcium Independent Mannose-6-Phosphate Receptor (CIMPR). In this subcellular compartment, the low pH (pH 4-4.5) and proteolysis would decrease or eliminate the interaction of antibody and rhASB.

A potential side effect of administration of enzyme replacement therapy (ERT) is the development of enzyme-specific antibodies in patients receiving multiple rounds of therapy. These enzyme-specific antibodies may precipitate potential adverse events and changes in clinical efficacy, including anaphylactoid-type reactions associated with antibodies of the IgE isotype, changes in pharmacokinetic profile, neutralization of the enzymatic activity in the lysosome, interference with receptor-mediated enzyme uptake, and breaking of tolerance toward self proteins. Reliable assays to accurately measure development of anti-enzyme antibodies would enable assessment of the treatment regimen in a patient receiving ERT and facilitate more efficient design of patient therapy (Mire-Sluis et al., *J. Immunological Methods* 289:1-16 (2004)). Thus, there remains a need in the art for reliable, sensitive assays that detect antibodies to lysosomal enzymes useful in enzyme replacement therapy.

SUMMARY OF INVENTION

The invention is based on the development of specific and selective assays for the measurement of antibodies associated with protein therapeutics, including enzyme replacement therapy for lysosomal storage disorders.

One aspect of the invention is a method for detecting lysosomal enzyme (LE)-specific antibodies in an animal (e.g., a human) comprising the steps of: (a) contacting a body fluid (e.g., serum) sample from the animal with a first lysosomal enzyme labeled with a capture moiety and a second lysosomal enzyme labeled with a detection moiety to form a LE-specific antibody/lysosomal enzyme complex, (b) capturing the LE-specific antibody/lysosomal complex from step (a) by contacting the LE-specific antibody/lysosomal complex with a solid support that specifically binds to the capture moiety, and (c) detecting the presence of LE-specific antibodies in the body fluid sample by detecting the presence of the second lysosomal enzyme labeled with the detection moiety.

A second aspect of the invention is a method for detecting lysosomal enzyme (LE)-neutralizing antibodies in an animal (e.g., a human) comprising the steps of: (a) isolating antibodies from phosphate and sulfate ions in a body fluid (e.g., serum) sample from the animal, (b) contacting the isolated antibodies from step (a) with a lysosomal enzyme to form a LE-specific antibody/lysosomal enzyme complex, (c) adding an enzyme substrate, and (d) detecting the amount of cleavage of the enzyme substrate by the lysosomal enzyme in the presence and absence of the isolated antibodies in the body fluid sample, wherein reduced cleavage in the presence compared to the absence of the isolated antibodies indicates the presence of LE-neutralizing antibodies in the body fluid sample.

A third aspect of the invention is a method for detecting antibodies that inhibit lysosomal enzyme (LE) uptake in an animal (e.g., a human) comprising the steps of: (a) incubating a body fluid (e.g., serum) sample from the animal with a lysosomal enzyme labeled with a detection moiety, (b) contacting the incubation mixture from step (a) with an LE receptor or an LE-binding fragment thereof, said LE receptor or LE-binding fragment thereof being bound to a solid support, (c) and detecting binding of the lysosomal enzyme labeled with the detection moiety from step (a) to the LE receptor or LE-binding fragment thereof, wherein a reduced binding in the presence of the body fluid sample as compared to binding in the absence of the body fluid sample indicates that the body fluid sample contains an antibody that inhibits LE uptake.

A fourth aspect of the invention is a method of detecting lysosomal enzyme (LE)-specific antibodies of IgE isotype in an animal (e.g., a human) comprising the steps of: (a) capturing IgE in a body fluid (e.g., serum) sample from the animal by contacting the body fluid sample with IgE-specific antibody bound to a solid support, (b) contacting the captured IgE from step (a) with a lysosomal enzyme labeled with a detection moiety, and (c) detecting the amount of IgE isotype LE-specific antibody in the body fluid sample by detecting the amount of the lysosomal enzyme labeled with the detection moiety.

DETAILED DESCRIPTION OF THE INVENTION

The present invention is based on the development of sensitive, specific assays to detect antibodies from patient body fluids and tissues specific for lysosomal enzymes.

Unless otherwise defined, all technical and scientific terms used herein have the same meaning as commonly understood by one of ordinary skill in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

As used herein, the following terms have the meanings ascribed to them unless specified otherwise.

The term "derivative" when used in connection with antibody substances and polypeptides of the invention refers to polypeptides chemically modified by techniques including, but not limited to, ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins. Derivatives retain the binding properties of underivatized molecules of the invention.

The terms "detectable moiety," "detection moiety" or a "label" as used herein refers to a composition detectable by means including, but not limited to, spectroscopic, photochemical, biochemical, immunochemical, chemical, or other physical means. For example, useful detectable moieties or labels include Ruthenium (Ru)-based catalyst, Europium, $^{32}P$, $^{35}S$, fluorescent dyes, electron-dense reagents, enzymes (e.g., as commonly used in an ELISA), biotin-Streptavidin, dioxigenin, haptens and proteins for which antisera or monoclonal antibodies are available, and nucleic acid molecules with a sequence complementary to a target. The detectable moiety or label often generates a measurable signal, such as a radioactive, chromogenic, luminescence, or fluorescent signal, which can be used to quantitate the amount of bound detectable moiety or label in a sample.

The term "capture moiety" as used herein refers to a composition that is capable of being specifically bound by another composition that is attached or linked to a solid support. Many of the above detection moieties can also be used as capture moieties so long as a binding event is involved. For example, useful capture moieties include affinity labels for which specific and selective ligands are available (e.g., biotin with avidin, glutathione with GST), haptens and proteins for which antisera or monoclonal antibodies are available (e.g., c-Myc), nucleic acid molecules with a sequence complementary to a target, and peptides for which specific and selective ligands are available (e.g., histidine tag with Ni). Molecules that affect the binding characteristics to a chromatographic resin are also envisioned. The solid support can be, for example, a filter, a plate, a membrane, a chromatographic resin, or a bead.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using a sequence comparison algorithm or by visual inspection.

The term "variant" as used herein refers to a polypeptide sequence that contains at least one amino acid substitution, deletion, or insertion in the coding region relative to the original polypeptide coding domains. Variants retain the biological activity of the naturally occurring polypeptide. For example, it is contemplated that a lysosomal enzyme used in the method of the invention may be the naturally occurring enzyme or may comprise one or more amino acid changes from the naturally occurring enzyme, but retains the biological activity of the enzyme. Likewise, a lysosomal enzyme receptor used in the method of the invention may be a variant or fragment of the naturally occurring receptor, but retains binding to its ligand.

The term "detectable lysosomal enzyme" as used herein generally refers to a lysosomal enzyme capable of being detected, e.g., the lysosomal enzyme reagent is directly labeled in addition to its inherent binding to a lysosomal enzyme-specific antibody.

The term "IgE-specific antibody" as used herein refers to an antibody having greater reactivity for an IgE isotype antibody, e.g., has minimal cross reactivity with other antibody isotypes such as IgG.

The term "limit of detection" or "LOD" or "sensitivity" as used herein generally refers generally to the lowest analyte concentration in a body fluid (e.g., serum) sample that can be detected but not necessarily quantitated as an exact value. For example, LOD may be defined as the analyte concentration that consistently generates a signal greater than the measured mean response of the pooled naïve matrix plus a cutpoint factor.

The term "cutpoint factor" or "threshold" as used herein generally refers to a value that is used to mathematically manipulate the signal from the naïve pooled matrix (e.g., serum) to set the minimum signal required from a sample to be considered positive. The cutpoint factor may be determined based on a confidence interval from a set of samples from individuals that have not been previously exposed to the therapeutic lysosomal enzyme. For example, the 95% confidence interval, calculated as 1.645 multiplied by the standard deviation across the individual samples, will lead to approximately a 5% false positive rate.

The term "interference" as used herein refers generally to the presence of substances in body fluid (e.g., serum) samples that prevent the target analyte from accurate detection and measurement. As used herein, interference refers generally to the effect of free drug or the effect of the matrix (e.g., serum) on the concentration-response relationship. For example, interference from matrix may be evaluated as the relative accuracy to samples without the potential interference to target a range of 75-125% relative accuracy.

The term "precision" as used herein generally refers to the variability in signal between the analysts and days. For example, precision may be evaluated as coefficient of variation, ranges of values, or using ANOVA statistics.

The term "reagent stability" as used herein generally refers to the robustness of preparation and storage stability of the reagents. For example, reagent stability may be established by the conditions that still permit values to be measured within 75-125% accuracy relative to freshly prepared reagents.

The term "sample stability" as used herein generally refers to the stability of the analyte in the biological fluid or tissue samples to handling conditions that the collected samples are anticipated to experience. Sample stability may be measured as the conditions that still permit values to be measured within 75-125% accuracy relative to freshly collected samples. For example, sample stability may be evaluated at −20° C. and −80° C. over time periods equal to a typical storage period, at RT or 4° C. over a time period equal to the typical sample preparation and analytical run times, at −20° C., 4° C. and RT over a time period equal to the typical shipping period, or through freeze-thaw cycles that may be experienced.

The term "robustness" as used herein generally refers to the capacity of the assay to remain unaffected by small variations in method parameters and indicates reliability of the assay during normal run conditions. For example, robustness can be evaluated as the percent change of reagent concentration, reagent volume, or incubation time that still generates signal within 75-125% accuracy relative to the nominal conditions.

The term "specificity" as used herein generally refers to the ability of the assay to detect antibodies that react with a specific protein. For example, specificity may refer to a proportional detection response with the specific analyte, while response from an antibody sample that is not specific for the lysosomal enzyme should be below the LOD. The proportional response may be evaluated against a correlation coefficient R value greater than or equal to 0.98.

The term "matrix" or "matrices" as used herein generally refers to the biological background in which the antibodies are measured. Examples of matrices include, for example, body fluid and tissue.

The term "body fluid" as used herein refers to a fluid that is obtained from a subject, e.g., human. For example, a body fluid may be blood, cerebrospinal fluid (CSF) or urine. The blood may be fractionated to remove cells (i.e., plasma) or fractionated to remove cells and clotting factors (i.e., serum).

The term "tissue" as used herein refers to tissues that are obtained from a subject, e.g., human. For example, a tissue may be from a biopsy sample, surgically removed tissue, or postmortem collection. Furthermore, the tissue may be homogenized and extracted to isolate the antibodies from the tissue.

The term "naïve" as used herein refers to individuals, e.g., humans, which have not been previously exposed to the LE therapeutic, but may have been exposed to endogenous levels.

Variants

In certain embodiments, lysosomal enzyme (LE) or LE receptor analogs and variants may be prepared and will be useful in a variety of applications in which lysosomal enzymes and their receptors may be used. LE or LE fragments include the full-length enzyme, or any variant, fragment or modification thereof that retains at least some of the biological activity (i.e., enzymatic activity) of the full-length enzyme. LE receptor or LE-binding fragments include full-length receptor, an extracellular portion of the receptor, or any variant, fragment or modification thereof that retains at least some of the biological activity (i.e., LE-binding activity) of the full-length LE receptor.

Full-length LE can be isolated from natural sources or prepared using recombinant techniques. LE fragments can be prepared using recombinant techniques. LE receptors can be isolated from natural sources (e.g., purified from fetal bovine serum) or prepared using recombinant techniques. For example, a general strategy to generate recombinant full-length LE receptors or extracellular portions of LE receptors, or variants or variants, fragments or modifications thereof that retains LE-binding activity is to amplify the coding region of interest from the LE receptor cDNA by PCR, clone the cDNA into a mammalian expression vector, transfect the mammalian expression vector into mammalian cells, e.g., Chinese hamster ovary (CHO) or G.7.1 cells, and purify the LE receptor using procedures to isolate LE receptors shed from cells present in fetal bovine serum. LE receptors or variants thereof can be from human or other mammalian sources.

Amino acid sequence variants of LE or LE receptors can be, for example, substitutional, insertional or deletion variants. Deletion variants lack one or more residues of the native LE or LE receptor, which are not essential for function and/or immunogenic activity. Insertional mutants typically involve the addition of material at a non-terminal point in the polypeptide. This may include the insertion of an immunoreactive epitope or simply a single residue. Terminal additions are additions of amino acid sequences at either the N— or C-terminus of the LE or LE receptor. Terminal additions can be used to improve the LE or LE receptor's biophysical characteristics or simplify the purification. Peptide additions include, for example and not for limitation, HIS (e.g., 6 or 12), TAT, FLAG™, HA, c-Myc, VSV-G, V5, S-peptide, and HSV. Protein additions include, for example and not for limitation, GFP, MBP, and GST.

Substitutional variants typically exchange one amino acid of the naturally occurring LE or LE receptor for another at one or more sites, and may be designed to modulate one or more properties of the LE or LE receptor, such as stability against proteolytic cleavage, without the loss of other functions or properties. Substitutions of this kind preferably are conservative, i.e., one amino acid is replaced with one of similar shape and charge.

Variants may be substantially homologous or substantially identical to the naturally occurring LE or LE receptor. In the context of two nucleic acids or polypeptides, substantially homologous generally refers to two or more sequences or subsequences that have at least 40%, 60%, 80%, 90%, 95%, 96%, 97%, 98% or 99% nucleotide or amino acid residue identity, when compared and aligned for maximum correspondence, as measured using sequence comparison algorithms well known in the art or by visual inspection.

Labels (Detectable and Capture Moieties)

In some embodiments, an assay reagent is labeled to facilitate its detection. A label or a detectable moiety is a composition detectable by spectroscopic, photochemical, biochemical, immunochemical, chemical, or other physical means. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), or luminescent or bioluminescent labels (such as Europium, Vanadium, etc.), paramagnetic atoms, electrochemiluminescent labels (such as Ru-based labels in conjunction with substrates, etc.), and the like.

In some embodiments, an assay reagent is labeled to facilitate its capture. A capture moiety is a composition that is capable of being specifically bound by another composition that is attached or linked to a solid support. An assay reagent, e.g., lysosomal enzyme, can be labeled through the use of affinity labels (such as biotin, avidin, etc.) for which specific and selective ligands are available, haptens and proteins for which antisera or monoclonal antibodies are available, and nucleic acid molecules with a sequence complementary to a target. Procedures for accomplishing such labeling are described in Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The solid support can be a filter, plate, membrane or bead, and the like.

Examples of labels suitable for use in the present invention include, but are not limited to, radioactive labels (e.g., $^{32}P$), fluorophores (e.g., fluorescein), electron-dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide. Also contemplated are a nanotag, a molecular mass bead, a magnetic agent, a nano- or microbead containing a fluorescent dye, a quantum dot, a quantum bead, a fluorescent protein, dendrimers with a fluorescent label, a micro-transponder, an electron donor molecule or molecular structure, or a light reflecting particle.

For example, labels contemplated for use with present invention include, but are not limited to, fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), biotin, and colorimetric labels such as colloidal gold, colored glass or plastic beads (e.g., polystyrene, polypropylene, latex, etc.), and luminescent or chemiluminescent labels (e.g., Europium (Eu), MSD Sulfo-Tag).

The label may be coupled directly or indirectly to the desired component of the assay. Preferably, the label in one embodiment is covalently bound to the biopolymer using an isocyanate or N-hydroxysuccinimide ester reagent for conjugation of an active agent according to the invention. In one aspect of the invention, the bifunctional isocyanate reagents of the invention can be used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecule (e.g., Streptavidin) molecule, which is either inherently detectable or covalently bound to a signal system, such as a detectable enzyme, a fluorescent compound, or a chemiluminescent compound, or to a solid support, such as a filter, a plate, a membrane or a bead, and the like The compounds useful in the method of the invention can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), europium, Texas Red, nicotinamide adenine dinucleotide, flavin adenine dinucleotide, etc. Chemiluminescent compounds suitable for use as labels include, but are not limited to, Europium (Eu), Samarium (Sm), luciferin and 2,3-dihydrophthalazinediones, e.g., luminol. Electrochemiluminescent compounds suitable for use as labels include, but are not limited to, MSD TAG, MSD Sulfo-TAG, BV-TAG, and BV-TAG Plus. For a review of various labeling or signal producing systems that can be used in the methods of the present invention, see U.S. Pat. No. 4,391,904.

Detection Methods and Kits

Where the label is radioactive, means for detection include a scintillation counter or photographic film, as in autoradiography. Where the label is a fluorescent label, exciting the fluorochrome with the appropriate wavelength of light and detecting the resulting fluorescence may detect it. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric labels may be detected simply by observing the color associated with the label. Other labeling and detection systems suitable for use in the methods of the present invention will be readily apparent to those of skill in the art. Such labeled modulators and ligands can be used in the diagnosis of a disease or health condition.

Chemiluminescent labels may be detected by observing the light emitted upon reaction of the label with substrate. Electrochemiluminescent labels may be detected by observing the light emitted upon reaction of the label with substrate in an electrical field.

In some embodiments, the labeled compositions useful in the methods of the invention are linked to a solid support, including but not limited to, filters, plates or membranes. It is further contemplated that the labeled compounds may be labeled and interact in solution. For example, the capture antibody may be labeled with a fluorescent resonance energy transfer (FRET) donor molecule and the target molecule is labeled with a FRET acceptor molecule such that the molecules are in proximity when binding occurs. Alternatively, the target molecule may be labeled with the FRET donor and the antibody molecule the FRET acceptor. Another possibility is to separate quenching and fluorescent molecule both present on the antibody or target when target and antibody hybridize. The target molecule is only close enough for its label to emit if it is interacting with the reagent. This produces a system where the molecule only emits when it interacts with the reagent (direct monitoring). A narrow band pass filter can be used to block all wavelengths except that of the molecule's label. FRET molecule pairs are commercially available in the art (e.g., from Invitrogen), and may be used according to the manufacturer's protocol. FRET emissions are detected using optical imaging techniques, such as a CCD camera.

Another method of detecting the antibody-antigen interactions is to label it with an electron donor. This donor label would give electrons to an electrical contact to which the reagent is bound. See, for example, Ghindilis, *Biochem Soc Trans.* 28:84-9, (2000) and Dai et al., *Cancer Detect Prev.* 29:233-40 (2005), which describe enzymes useful in and methods for electro immunoassays. The electron contact would then be read by an A to D (analog to digital) converter and quantified. The higher the electron count the more interactions took place.

One embodiment of a label capable of single molecule detection is the use of plasmon-resonant particles (PRPs) as optical reporters, as described in Schultz et al., *Proc. Natl. Acad. Sci. USA* 97:996-1001 (2000), incorporated herein by reference. PRPs are metallic nanoparticles, typically 40-100 nm in diameter, which scatter light elastically with remarkable efficiency because of a collective resonance of the conduction electrons in the metal (i.e., the surface plasmon resonance). The magnitude, peak wavelength, and spectral bandwidth of the plasmon resonance associated with a nanoparticle are dependent on the particle's size, shape, and material composition, as well as the local environment. By influencing these parameters during preparation, PRPs can be formed that have scattering peak anywhere in the visible range of the spectrum. For spherical PRPs, both the peak scattering wavelength and scattering efficiency increase with larger radius, providing a means for producing differently colored labels. Populations of silver spheres, for example, can be reproducibly prepared for which the peak scattering wavelength is within a few nanometers of the targeted wavelength, by adjusting the final radius of the spheres during preparation. Because PRPs are bright, yet nanosized, they are used as indicators for single-molecule detection; that is, the presence of a bound PRP in a field of view can indicate a single binding event.

In one exemplary embodiment, the assay device is a lateral flow test strip, optionally encased in a housing. A first labeled antibody to a lysosomal enzyme is in solution, while a second antibody to a lysosomal enzyme is immobilized on the test strip. When a patient sample containing a lysosomal enzyme is contacted with both antibodies, an antibody-target-antibody sandwich complex is formed, and the resulting complex, which is immobilized on the solid support, is detectable by virtue of the label. The test strip is then inserted into a reader, where the signal from the label in the complex is measured. The outcome may be either a positive or negative result, or a quantitative determination of the concentration of a lysosomal enzyme in the sample, which is correlated with a result indicative of a risk or presence of a disease or disorder. The entire procedure may be automated and/or computer-controlled. Alternatively, the test strip may be read visually by comparison to a visual standard of the appropriate color. This test provides similar clinically relevant information as a lysosomal enzyme ELISA, but in significantly less time and at the point of care.

Antigen-antibody complexes may also be detected using nanoparticle-derived techniques. See, for example, Ao et al., *Anal Chem.* 78:1104-6 (2006), which describes gold nanoparticle quenching, Tang et al., *Biosens Bioelectron.* Nov. 30, 2005 which describes $SiO(2)/Au$ nanoparticle surfaces in antibody detection, and Lieu et al., *J Immunol Methods.* 307: 34-40 (2005), which describes silicon dioxide nanoparticles containing dibromofluorescein for use in solid substrate-room temperature phosphorescence immunoassay (SS-RTP-IA).

Kits are also contemplated within the scope of the invention. In one embodiment, the kit comprises a lysosomal enzyme, optionally linked to a detectable label or a capture moiety, and/or an antibody standard that specifically binds to the lysosomal enzyme, and/or a lysosomal enzyme standard containing a known quantity of a lysosomal enzyme. In another embodiment, the kit comprises a lysosomal enzyme substrate, and/or a lysosomal enzyme standard containing a known quantity of a lysosomal enzyme, and/or an antibody standard that specifically binds to, and neutralizes the enzymatic activity of, the lysosomal enzyme. In another embodiment, the kit comprises a lysosomal enzyme, optionally linked to a detectable label, and/or a lysosomal receptor that specifically binds to the lysosomal enzyme, and/or an antibody standard that specifically binds to, and blocks binding of the lysosomal receptor to, the lysosomal enzyme. In another embodiment, the kit comprises a lysosomal enzyme, optionally linked to a detectable label, and/or an antibody that specifically binds to antibodies of IgE isotype, and/or an antibody standard that specifically binds to the lysosomal enzyme, and/or a lysosomal enzyme standard containing a known quantity of a lysosomal enzyme. Other components of the kits may optionally include reagents and/or instructions for carrying out immunoassays, as described supra.

Spectral absorption labels may also be used. A possible methodology for detection would be to mix into the bead polymer different materials that absorb and pass different spectra of light. Each different type of bead could be detected by passing a multi-spectral light though the bead and detecting which spectra are absorbed.

Lysosomal Enzymes

Lysosomal enzymes are useful as therapeutics, for example, in the treatment of lysosomal storage diseases such as Aspartylglucosaminuria, Cholesterol ester storage disease/ Wolman disease, Cystinosis, Danon disease, Fabry disease, Farber Lipogranulomatosis/Farber disease, Fucosidosis, Galactosialidosis types I/II, Gaucher disease types I/II/III Gaucher disease, Globoid cell leukodystrophy/Krabbe disease, Glycogen storage disease II/Pompe disease, GM1-Gangliosidosis types I/II/III, GM2-Gangliosidosis type I/Tay-Sachs disease, GM2-Gangliosidosis type II Sandhoff disease, GM2-Gangliosidosis, alpha-Mannosidosis types I/II, alpha-Mannosidosis, Metachromatic leukodystrophy, Mucolipidosis type I/Sialidosis types II/I Mucolipidosis types II/III I-cell disease, Mucolipidosis type IIIC pseudo-Hurler polydystrophy, Mucopolysaccharidosis type I (MPS I), Mucopolysaccharidosis type II Hunter syndrome (MPS II), Mucopolysaccharidosis type IIIA Sanfilippo syndrome (MPS IIIA), Mucopolysaccharidosis type IIIB Sanfilippo syndrome (MPS IIIB), Mucopolysaccharidosis type IIIC Sanfilippo syndrome (MPS IIIC), Mucopolysaccharidosis (MPS) type IIID Sanfilippo syndrome (MPS IIID), Mucopolysaccharidosis (MPS) type IVA Morquio syndrome (MPS IVA), Mucopolysaccharidosis type IVB Morquio syndrome (MPS IVB), Mucopolysaccharidosis type VI (MPS VI), Mucopolysaccharidosis type VII Sly syndrome (MPS VII), Mucopolysaccharidosis type IX (MPS IX), Multiple sulfatase deficiency, Pompe Disease, Neuronal Ceroid Lipofuscinosis, CLN1 Batten disease, Neuronal Ceroid Lipofuscinosis, CLN2 Batten disease, Niemann-Pick disease types A/B Niemann-Pick disease, Niemann-Pick disease type C1 Niemann-Pick disease, Niemann-Pick disease type C2 Niemann-Pick disease, Pycnodysostosis, Schindler disease types I/II Schindler disease, and Sialic acid storage disease, Metachromatic Leukodystrophy, Gaucher, Krabbe, and Tay-Sachs disease wherein a lysosomal protein deficiency contributes to the disease state. In particularly preferred embodiments, the lysosomal storage disease is MPS VI. In another preferred embodiment, the lysosomal storage disease is Pompe Disease.

In a particular embodiment, the invention provides methods for detecting antibodies to a therapeutic protein having a biological activity which is reduced, deficient, or absent in the target lysosome and which is administered to the subject Preferred therapeutics include, but are not limited to aspartylglucosaminidase, acid lipase, cysteine transporter, Lamp-2, alpha-galactosidase A, acid ceramidase, alpha-L-fucosidase, beta-hexosaminidase A, GM2-activator deficiency, alpha-D-mannosidase, beta-D-mannosidase, arylsulfatase A, saposin B, neuraminidase, alpha-N-acetylglucosaminidase phosphotransferase, phosphotransferase γ-subunit, alpha-L-iduronidase, iduronate-2-sulfatase, heparan-N-sulfatase, alpha-N-acetylglucosaminidase, acetylCoA:N-acetyltransferase, N-acetylglucosamine 6-sulfatase, galactose 6-sulfatase, alpha-galactosidase, N-acetylgalactosamine 4-sulfatase, hyaluronoglucosaminidase, palmitoyl protein thioesterase, tripeptidyl peptidase I, acid sphingomyelinase, cholesterol trafficking, cathepsin K, beta-galactosidase B, α-glucosidase, and sialic acid transporter. In a preferred embodiment, alpha-L-iduronidase, α-glucosidase or N-acetylgalactosamine 4-sulfatase is the enzyme.

Antibody Purification

Antibodies may be purified using techniques standard in the art, including but not limited to protein A-Sepharose, hydroxylapatite chromatography, gel electrophoresis, dialysis, or affinity chromatography. The antibody composition prepared from microbial or mammalian cells or serum can be purified using, for example, hydroxylapatite chromatography cation or anion exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62: 1-13 (1983)). Protein G is recommended for all mouse isotypes and for human γ3 (Guss et al., *EMBO J.* 5:1567-75 (1986)). The matrix to which the affinity ligand is attached is most often agarose or acrylamide, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Solid Support Materials

For the methods of the invention, the antibody or lysosomal enzyme may be bound to a variety of solid supports, including but not limited to filters, PVC membranes, PDVF membranes, PVC plates and other plates which bind protein, microcarriers, macro solid phase beads, magnetic beads, made out of for example, polystyrene, nanoparticles, such as bimetallic silver-gold nanoparticles (Yan Cui et al., *J. Phys. Chem. B* 110 (9):4002-06 (2006), and polyamide membrane (PAM) sheets (Sun et al., *Analytical Letters* 34:1627-37 (2001)).

For example, microspheres with multiple fluorescent molecular fillings, different materials, surface texture, surface patterns, etc., can be utilized as identification tags. It is contemplated that either the capture antibody or the lysosomal enzyme is covalently bound to the bead and reacted against the opposite binding partner to assay the amount of lysosomal enzyme-specific antibody in serum. See, for example, Current Protocols in Immunology, Unit 6.11, 2006). Fluorescently filled microspheres are currently available from Molecular Probes, Inc. and other companies. Microspheres as small as 20nm diameter polystyrene beads are currently available.

The lysosomal enzymes or antibodies are attached to the solid support using standard protocols in the art, e.g., as described by the manufacturer of the support, or using standard chemical crosslinking techniques known in the art. See e.g., Pierce Biotechnology, Inc. (Rockford, Ill.) crosslinking kits.

1. Assay to Detect Lysosomal Enzyme-Specific Antibodies

Most protein therapeutics elicit some level of antibody response. In some cases this antibody response may lead to serious side effects or loss of efficacy. Here the goal was to develop an assay that can detect the total antibody response to the lysosomal enzyme (LE), regardless of the specific antibody Ig isotype or subclass.

In the first aspect, the invention contemplates a method to detect antibodies specific against lysosomal enzymes (LEs) in an animal (e.g., a human) comprising the steps of: (a) contacting a body fluid (e.g., serum) sample from the animal with a first lysosomal enzyme labeled with biotin and a second lysosomal enzyme labeled with a detection moiety to form a LE-specific antibody/lysosomal enzyme complex, (b) capturing the LE-specific antibody/lysosomal enzyme complex from step (a) with a Streptavidin coated plate, and (c) detecting the presence of captured LE-specific antibody in the body fluid sample by detecting the presence of the second lysosomal enzyme labeled with the detection moiety.

In one embodiment, the invention contemplates a bridging immunoassay to detect antibodies specific against recombinant human arylsulfatase B (rhASB) independent of Ig isotype and host species, tolerant of free drug in the body fluid, and with ng/mL sensitivity. To test the immunogenicity of the enzyme, an electrochemiluminescence assay (ECLA) bridged format was implemented to develop a more sensitive assay with improved tolerance to free drug in the body fluid (e.g., serum) samples. The bridged format takes advantage of the bivalency of the antibody analyte by preparing the lysosomal enzyme with separate capture and detection moieties or agents. This assay format detects antibodies regardless of the species or isotype. The simultaneous solution phase incubation of detection and capture reagents provides the ability to use long incubations to reduce interference from free drug by allowing exchange of reagents with any free drug bound to the antibodies in the body fluid (e.g., serum) samples. Because the assay format incorporates fewer washes, the assay is theoretically able to detect lower affinity antibodies.

A critical aspect to develop a suitable LE-specific antibody assay was to find a way to label the LE with a detection moiety or a capture moiety in a manner that optimizes sensitivity while minimizing the number of epitopes that are blocked. To accomplish this, multiple labeling chemistries and challenge ratios were evaluated to generate a range of labeling ratios in the final product. To ensure that the fewest numbers of epitopes were masked, the lowest labeling ratio that generated adequate signals was selected.

Two benefits of the Streptavidin-biotin interaction are its strength and specificity. These properties make this pairing an excellent option for the capture moiety, however, the strength of binding poses an assay development challenge because the interaction of the LE labeled with a biotin capture moiety with the Streptavidin-coated solid support sequesters the capture LE out of solution. The kinetics of binding changes in the solid phase, so that an optimized ratio of detection LE and capture LE no longer generates an adequate signal. To minimize this effect, the preincubation step of body fluid and LE reagents was separated from the capture step on the Streptavidin plate, and the two incubation steps were optimized separately. An alternative approach would be to specifically optimize the reagent ratios for the mixed solid phase/solution phase interactions.

In a preferred embodiment, the bridging assay is developed on the MesoScale Discovery (MSD) Sector PR400 plate reader. The bridging assay uses two rhASB reagents, one labeled with biotin, and the other labeled with MSD Sulfo-Tag. For the assay, rhASB is prepared with a tag or label such as biotin (biotin-rhASB, Pierce EZ-Link) for capture and a second tag, e.g., ruthenium (MSD Sulfo-TAG NHS-Ester) for detection. A signal is generated in the ECL format when an antibody binds one biotin-rhASB and one Ru-rhASB. The body fluid (e.g., serum) is incubated with the labeled rhASB overnight prior to incubation on a Streptavidin plate to reduce interference from free drug present in body fluid samples. To confirm positive results, the body fluid samples are incubated with excess unlabeled rhASB to confirm a specific interaction via a reduction in signal. The reported value is a titer value corresponding to the highest dilution factor that remains positive.

The assay can be used to detect LE-specific antibodies in a body fluid or tissue sample from a subject. In a preferred embodiment, the body fluid is serum. In another embodiment, the body fluid is cerebrospinal fluid (CSF).

In an alternative embodiment, the capture rhASB is labeled with a first fluorescent label, and the detection rhASB, which may be pre-bound to serum antibodies, is labeled with a second fluorescent label, the first and second fluorescent labels chosen so that a detection device generates a signal when the two are in very close proximity, i.e., linked in the same complex with the rhASB-specific antibody from the body fluid.

In another alternative embodiment, the capture rhASB is bound to a solid support rather than labeled with a second label. Although this format brings the binding reaction into solid phase rather than solution phase, it does still present the opportunity to bind multiple Ig isotypes from multiple species.

In another embodiment, the invention contemplates a bridging immunoassay to detect antibodies specific against another lysosomal enzyme, recombinant human α-glucosidase (rhGAA), independent of Ig isotype and host species, tolerant of free drug in the body fluid, and with ng/mL sensitivity.

In an alternative embodiment, the capture rhGAA is labeled with a first fluorescent label, and the detection rhGAA, which may be pre-bound to serum antibodies, is labeled with a second fluorescent label, the first and second fluorescent labels chosen so that a detection device generates a signal when the two are in very close proximity, i.e., linked in the same complex with the rhGAA-specific antibody from serum.

In yet another alternative embodiment, the capture rhGAA is bound to a solid support rather than labeled with a second label. Although this format brings the binding reaction into solid phase rather than solution phase, it does still present the opportunity to bind multiple Ig isotypes from multiple species.

2. Assay to Detect Lysosomal Enzyme (LE)-Neutralizing Antibodies

Because the low pH (pH 4-4.5) and proteolysis in the lysosomal compartment could decrease or eliminate the interaction of antibody and lysosomal enzymes, such as rhASB, it is unlikely that an anti-LE antibody would directly inhibit enzymatic activity. However, the potential to neutralize activity exists and would interfere with the efficacy of enzyme therapy. Here, the goal was to develop an assay to detect neutralizing antibodies directed against a lysosomal enzyme (LE) administered as part of an enzyme replacement therapy in a patient in which the antibodies isolated from the patient retain their ability to bind LE under conditions in which the bound therapeutic protein has enzymatic activity.

A second aspect of the invention is a method for detecting lysosomal enzyme (LE)-neutralizing antibodies in an animal (e.g., a human) comprising the steps of: (a) isolating antibodies from phosphate and sulfate ions in a body fluid (e.g., serum) sample from the animal, (b) contacting the isolated antibodies from step (a) with a lysosomal enzyme to form a LE-specific antibody/lysosomal enzyme complex, (c) adding an enzyme substrate, and (d) detecting the amount of cleavage of enzyme substrate by the lysosomal enzyme in the presence and absence of the isolated antibodies in the body fluid sample, wherein reduced cleavage in the presence compared to the absence of the isolated antibodies indicates the presence of LE-neutralizing antibodies in the body fluid sample.

One preferred embodiment is a neutralizing antibody assay designed to determine if the enzymatic activity of rhASB is inhibited by human serum that contains antibodies that bind rhASB. The serum contains multiple ions, such as phosphate and sulfate, which interfere with measuring sulfatase activity through product inhibition. Removal of these interfering substances can be accomplished by isolating the antibody fraction from the serum matrix through an affinity separation under conditions that allow maximal recovery of antibodies with rhASB-binding activity. In a preferred embodiment, this is accomplished by using a resin conjugated to Protein A/G. In alternative embodiments, removal of interfering substances can be accomplished using a resin conjugated to other proteins or combinations of proteins with Ig domain binding characteristics, including, but not limited to, Protein A, Protein L, Protein A/L, and Protein G/L. After isolation of the antibodies from serum, conditions are identified that allow formation of antibody-LE complexes under which the LE retains enzyme activity. A preincubation step with LE allows for antibody-LE complexes to form before exposure to the enzyme substrate. In a preferred embodiment, the substrate is a synthetic fluorogenic substrate. In alternative embodiments, the substrate can be polysaccharides from synthetic or natural sources that contain specific substrates.

A challenge in developing an appropriate antibody purification procedure was to identify a method with suitable capacity and robustness. A wide number of supports, including magnetic beads, high-protein binding plates, discs and chromatographic resins, were investigated. The method that showed the highest recovery mass with good repeatability was a polyacrylamide resin with Protein A/G bound.

Once the resin was selected, a method needed to be developed to elute and neutralize the antibodies to a suitable condition (i.e., pH, salt concentration, etc.) for the enzymatic reaction. A challenge was to identify antibody elution conditions that minimized the retention of phosphate and sulfate ions. Extensive investigation with combinations of PBS and deionized water was used to identify conditions with high antibody retention and minimal retention of phosphate on the resin.

An additional challenge was to identify neutralization conditions that would be acceptable for the subsequent enzymatic reaction. The standard neutralization with Tris to neutral pH was not acceptable because the enzymatic reaction needs to be performed at around pH 5.6 for good reproducibility. Multiple buffers were tested to identify an appropriate candidate that met the criteria of minimal interference with the enzymatic assay and maximum robustness in attaining the same final pH, even with slight perturbations in the ratio of glycine elution buffer and basic neutralization conditions. Different elution buffers were tried to replace the standard glycine elution buffer, but changing this buffer resulted in decreased robustness of antibody elution.

The assay can be used to detect LE neutralizing antibodies in a body fluid or tissue sample from a subject. In a preferred embodiment, the body fluid is serum.

3. Assay to Detecting Antibodies that Inhibit Lysosomal Enzyme (LE) Uptake

Neutralizing antibodies that interfere with binding of a therapeutic with its receptor would limit the uptake of the drug thereby interfering with the efficacy of the drug treatment. Thus there remains a need in the art to develop a method to detect antibody mediated receptor ligand neutralization. Here, the goal was to develop an assay to detect antibodies that inhibit LE receptor-mediated LE uptake when the LE itself has multiple epitopes that can be used for binding to its cognate LE-receptor.

A third aspect of the invention is a method for detecting antibodies that inhibit lysosomal enzyme (LE) uptake in an animal (e.g., a human) comprising the steps of: (a) incubating a body fluid (e.g., serum) sample from the animal with a lysosomal enzyme labeled with a detection moiety, (b) contacting the incubation mixture from step (a) with an LE receptor or an LE-binding fragment thereof, said LE receptor or fragment thereof being bound to a solid support, and (c) detecting binding of the lysosomal enzyme labeled with the detection moiety from step (a) to the LE receptor or fragment thereof, wherein a reduced binding in the presence of the body fluid sample as compared to binding in the absence of the body fluid sample indicates that the body fluid sample contains an antibody that inhibits LE uptake.

A preferred embodiment is a method of detecting rhASB antibodies that inhibit the interaction of the LE with the human mannose-6-phosphate receptor. An alternative embodiment is a method of detecting rhASB antibodies that inhibit the interaction of the LE with the other mammalian mannose-6-phosphate receptors. The use of a receptor-binding assay can be a surrogate for a cellular uptake assay as prior work has established that receptor binding is necessary and sufficient for uptake (Dintzis et al., *J Biol Chem* 269:12159-66 (1994)). A significant hurdle to overcome in this method is that recombinant rhASB, like other lysosomal enzymes, has multiple mannose-6-phosphate residues that can mediate binding to, and, hence, uptake by, the mannose-6-phosphate receptor. A preincubation step for the LE and antibodies ensures that antibody complexes have the opportunity to form prior to exposing the complexes to the receptor.

A major challenge in developing this assay was to determine a combination of LE receptor and LE concentrations that allowed measurement of small changes in binding. The LE receptor concentration was selected so that the LE receptor binding curves mimicked the binding curves for a cell line. To keep the detectable LE signal level at 100% high, a LE concentration was selected that generated a signal at half the maximum binding signal for the LE receptor concentration. This LE concentration allowed measurement of inhibition along the steep portion of the binding curve. The conditions were confirmed by comparing inhibition of binding to cells and the plate.

The assay can be used to detect antibodies that inhibit LE uptake in a body fluid or tissue sample from a subject. In a preferred embodiment, the body fluid is serum.

4. Assay to Detect Lysosomal Enzyme (LE)-Specific Antibodies of IgE Isotype

Elevated drug-specific IgE antibodies can be observed in some human patients who have exhibited hypersensitivity reactions to drug administration. Extreme allergic reactions such as anaphylaxis may be associated with IgE-mediated histamine release or other cellular mechanisms. In an allergic reaction, the important analyte is not total serum IgE, but rather a fraction of the total IgE that is capable of binding the administered drug, e.g., rhASB, during enzyme replacement therapy for MPS VI disease. Here, the goal was to develop an assay to detect LE-specific IgE isotype antibodies when the majority of the antibodies, in particular LE-specific antibodies, e.g., anti-rhASB antibodies, in the body fluid of the patient are of different isotype, in particular, the IgG isotype.

A fourth aspect of the invention is a method of detecting lysosomal enzyme (LE)-specific antibodies of IgE isotype in an animal (e.g., a human) comprising the steps of: (a) capturing IgE in a body fluid (e.g., serum) sample from the animal by contacting the body fluid sample with IgE-specific antibody bound to a solid support, (b) contacting the captured IgE from step (a) with a lysosomal enzyme labeled with a detectable moiety, and (c) detecting the amount of IgE isotype LE-specific antibodies in the body fluid sample by detecting the amount of the lysosomal enzyme labeled with the detection moiety.

Although significant allergic reactions to intravenous infusions of rhASB among MPS VI patients are rare, there is a need for a laboratory assay that can determine whether rhASB specific IgE antibodies are present in body fluids (e.g., serum) at levels significantly greater than background levels exhibited by individuals not receiving the drug. Nominal levels of total nonspecific IgE in human serum are extremely low (20-400 ng/mL), in comparison to IgG (6-13 mg/mL). These values can result in up to 650,000-fold difference in total IgG to total IgE. Therefore, the presence of LE-specific IgG is potentially a significant barrier to detecting LE-specific IgE. To minimize this interference, the first step of this assay captures the total IgE fraction from serum onto a solid support, rather than a typical assay in which LE-specific antibodies of any isotype are captured from serum by binding to the target protein bound to the solid support. The subsequent detection with labeled LE allows measurement of the subfraction of total IgE that is specific for LE, rather than the measurement of the subset of LE-specific antibodies that are of the IgE isotype. A preferred embodiment is a method for detecting the presence of rhASB-specific IgE antibodies in human serum based on reversed immunoassay (anti-rhASB IgE ELISA).

To minimize the impact of specific IgG on the assay format, multiple anti-human IgE antibodies were screened against curves of human IgG and human IgE to determine the relative sensitivity. The best antibody detected IgE at 0.41 ng/mL more strongly than IgG at 300 ng/mL, corresponding to an at least about 730-fold greater binding affinity for IgE. Since only a fraction of IgG inadvertently captured will be specific to the LE, this level of cross-reactivity is acceptable.

In an alternate embodiment, an indirect immunoassay is employed. This format involves the binding of rhASB to an ELISA multiwell plate, binding of a serum sample to the rhASB, and detection by HRP-conjugated anti-human IgE or biotinylated anti-human IgE and Streptavidin-HRP. This format was more sensitive to interference from anti-rhASB IgG, so may be unsuitable for this specific application.

In another alternative embodiment, the IgE-specific antibody is not bound to a solid support, but is linked to a second label that is detectable when in proximity to the detectable lysosomal enzyme label, and the two reagents are allowed to react in solution. In one exemplary embodiment, the IgE-specific antibody is labeled with a first fluorescent label, and the detectable lysosomal enzyme, which may be bound to serum antibodies, is labeled with a second fluorescent label, the first and second fluorescent labels chosen so that a detection device gives a signal when the two are in very close proximity, i.e., linked in the same complex with the lysosomal enzyme (LE)-specific antibody.

The assay can be used to detect LE-specific antibodies of IgE isotype in a body fluid or tissue sample from a subject. In a preferred embodiment, the body fluid is serum.

Having now generally described the invention, the same may be more readily understood through the following reference to the following examples. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLES

Example 1

Detection of Human Arylsulfatase B-Specific Antibodies from Serum

The purpose of this assay development was to create a method to assess the immunogenicity of recombinant human arylsulfatase B (rhASB).

Antibodies used to develop the assay include polyclonal antibodies, all of which were purified using a Protein G column followed by rhASB affinity chromatography. The four species studied were sheep (G192), rabbit (BP15), cynomolgus monkey (pool), and human (pool). To test specificity, a rabbit polyclonal antibody against recombinant human alpha-L-iduronidase (anti-rhIDU) was used to ensure that the bridging format did not measure antibodies against other LE.

Sample dilutions and stocks of Ru-rhASB and biotin-rhASB were prepared in 2% Blocker A [2% bovine serum albumin (BSA) in phosphate buffered saline (PBS)]. Equal volumes of Ru-rhASB, biotin-rhASB, and sample dilutions were mixed in a preincubation plate. The preincubation plate was incubated at room temperature (RT). The Streptavidin assay plate was blocked with 150 µL per well 5% Blocker A at RT or 4° C. The block was shaken out of the assay plate and 50 µL of each mixture was transferred to the blocked Streptavidin assay plate. The assay plate was incubated at RT, washed 3× PBS-Tween, and 150 µL per well of Read Buffer T was added. The plate was read in the Sector PR 400.

For the screening assay, the reagents were first preincubated in a low-binding white 96-well plate, 30 µL 4 µg/mL Ru-rhASB, 30 µL 4 µg/mL biotin-rhASB and 30 µL 1:10 dilutions of controls and samples were added to each well. The preincubation plate was sealed with foil seal and incubated at RT on a plate shaker overnight. The MSD Streptavidin plate (assay plate) was blocked with 150 µL of 5% blocking buffer (5% BSA) (MSD Blocker A) at 4° C. overnight. The following day, the solution in the Streptavidin assay plate was discarded and 50 µL per well transferred from preincubation plates to the assay plate. The assay plate was sealed and incubated for 30 minutes at RT on a plate shaker. The plate was then washed three times with wash buffer. 150 µL of 2× Read Buffer T (MesoScale Discovery) was added to each well and the assay plate read at the appropriate wavelength. The signals from each sample and control were compared to the signal from the 1:10 dilution of the pool.

For the confirmatory assay, the screening protocol was followed except two separate 1:10 dilutions of samples were prepared in either 2% Blocker A or 100 µg/mL rhASB in 2% Blocker A prior to incubation with the labeled rhASB reagents. The signal of samples diluted in Blocker A containing rhASB were compared to the signal of samples diluted in Blocker A alone.

For the titer assay, the screening protocol was followed except the 1:10 dilutions of samples were also serially diluted 3-fold prior to incubation with the labeled rhASB reagents. The signal of each dilution was compared to the signal from the 1:10 dilution of the pool.

Separating the total incubation time between the preincubation step and the Streptavidin plate incubation resulted in higher signals relative to background. An about 30 min incubation time on the Streptavidin assay plate was selected to minimize background without much sacrifice on signal. The preincubation was optimized to an overnight incubation for an increased signal at lower antibody concentrations without significant increase in background.

Labeling rhASB with Biotin and Ru

RhASB was buffer exchanged into labeling buffer (10 mM sodium phosphate, 150 mM NaCl, pH 7.8) and concentrated to 2 mg/mL. Just before labeling, stocks of MSD Sulfo-tag and biotin were prepared. The MSD tag and biotin stocks were added at 1.25 to 12-fold molar excess challenge ratios.

The tubes were incubated for 1 hour at RT on the Vari-Mix rocker. The reactions were quenched with 20-25% v/v 2 M glycine, and then buffer exchanged into the original formulation buffer both for reagent stability and to remove free tag. The rhASB concentration was determined using Pierce BCA kit in mg/mL and converted to molar concentration using the MW 59687 g/mol.

To quantitate the extent of Ru quantitation, the absorbance at 455 nm was measured and the molar concentration of Ru was calculated using the extinction coefficient 15400 $M^{-1}cm^{-1}$.

To quantitate the biotin labeling, a HABA/Avidin method was employed.

To improve the accuracy in measuring the extent of biotin incorporation, a chromogenic biotin product was also investigated (Pierce EZ-Link NHS-Chromogenic Biotin). In preliminary experiments, the two different forms of biotin-rhASB behaved similarly, but full characterization of the chromogenic form was not conducted.

Optimization of reagent preparation required significantly decreasing the challenge ratio from standard conditions. Experiments demonstrated that a challenge ratio of about 2.5 for both biotin-rhASB and Ru-rhASB yielded a label ratio of about 1.5, providing a balance from requiring labels on rhASB to obtain signal while minimally altering rhASB to avoid masking epitopes. Although differences in conditions were moderate, the least difference from signal to background was obtained when the two reagents were used in about equimolar ratios, as expected since signal is only obtained when an antibody binds one Ru-rhASB and one biotin-rhASB.

Establishment of Assay Cutpoint

To determine the signal that will result in a positive assay result using naïve sera from multiple individuals (cutpoint), the average assay signal for multiple naïve individuals was calculated from three replicates and standard deviation was calculated from the individual averages. The standard deviation was multiplied by 1.645, i.e., the t-factor for a one-tailed 95% confidence interval. The cutpoint was set at a 95% confidence interval to provide a 5% false positive rate.

Cutpoint factors were established by assaying 50 naïve human sera or CSF. For rabbit serum, rat serum, feline serum, and feline CSF, cutpoint factors were established by assaying 20 naïve samples. The standard deviation between the average signals for the individual human sera was very close to the system variability (SD=14-18), indicating that variations for individual sera are not a significant factor for the assay. Similar distributions were observed for all additional matrices tested.

Sensitivity

To determine the lowest analyte concentration in serum that can be detected in this assay, but not necessarily quantitated, purified antibodies were prepared at 50-100,000 ng/mL in naïve pooled serum. The signal from 1:10 dilutions of prepared concentrations were compared to the signal from a 1:10 dilution of naïve pooled serum.

The limit of detection varied depending on the source of the polyclonal antibody, with better than about 250 ng/mL detection for all four sources. The assay was capable of detecting at least as low as about 50 ng/mL sheep polyclonal antibody G192 in neat serum, which corresponds to about 1.7 ng/mL final concentration of antibody in the assay mixture. An alternate embodiment could use a monoclonal antibody as a control for a more continuous supply of materials. The detection of antibodies isolated from multiple species confirmed that the bridging assay was capable of detecting antibodies with different constant domains.

Interference by Free Drug

To evaluate the effect of the free drug on the concentration-response relationship, affinity purified human anti-rhASB was prepared at 0.5-50 μg/mL in naïve human serum containing 0-100 ng/mL rhASB. Signals from 1:10 sample dilutions were compared to the 1:10 dilution of naïve serum, in a total volume of 150 μL. The limit of detection was compared for different serum concentrations of rhASB.

Prior pharmacokinetic analysis has demonstrated that at the 5 hr time point after 24 weeks of infusion therapy, no patient had more than 663 ng/mL rhASB present in plasma and more than half had less than 100 ng/mL rhASB. The concentration at day 7 post-infusion, the time when the serum samples were collected, was anticipated to be lower than 1 ng/mL. The limit of detection was established for concentrations in up to 10 μg/mL in the event that a patient has an antibody response that extends the PK curve. Sensitivity of at least about 500 ng/mL in neat serum was maintained with up to 10 μg/mL rhASB in neat serum.

In addition, the signal from 1:10 sample dilutions into 100 μg/mL rhASB was compared to the signal from 1:10 sample dilutions into 2% Blocker A. Although the assay was tolerant of free drug, the presence of 100 μg/mL rhASB in the sample diluent was able to serve as a confirmatory test for positive results. This would correspond to a 1 mg/mL serum concentration, which was unlikely to occur in actual patient samples since that is the concentration of the drug formulation.

Interference by Matrix

To evaluate the effect of the matrix (i.e., human serum) on the concentration-response relationship, affinity-purified polyclonal antibody was prepared at 50-50,000 ng/mL in naïve pooled serum, in 10% serum, and in 2% Blocker A. Signals from 1:10 sample dilutions were compared across the different serum concentration. Accuracy near the limit of detection was between 96-110%. Although more variable at higher concentrations, this variability can be tolerated since the reported value is a titer value and will be determined from dilutions yielding antibody concentrations near the limit of detection.

In addition to human serum, the above assay has also been qualified or validated in human cerebrospinal fluid, rabbit serum, rat serum, feline serum, and feline CSF. In all of these matrices, the matrix interference was significantly less than the ELISA format, with 10% matrix or higher tolerated in all formats.

The most marked improvement for this format versus ELISA was observed for feline serum. In all ELISA formats tested, the minimum dilution factor for feline serum was at least 100 to eliminate background to the level of 0% serum. In addition, nonspecific binding is a marked challenge for the rhASB ELISA, with many animals demonstrating high signals that cannot be competed with free LE. The solution phase bridging assay described here does not show these high and variable nonspecific signals.

Robustness

Variation in the reagent used (3.5-4.5 μg/mL Ru-rhASB and biotin-rhASB) and incubation times (14-22 hr preincubation times, and 20-40 min Streptavidin assay plate incubation times) were used to evaluate the robustness of the assay. Results showed that small variations in reagent concentrations did not affect the higher controls significantly, but did cause the 100 ng/mL control to fall below the cutpoint if the biotin-ASB concentration was higher than the Ru-ASB concentration. If this condition occurred during sample analysis, the plate would be disallowed due to failure to detect the low positive control. The preincubation time could range from 16 hr to 22 hr without significant changes in signal for all controls; the incubation on the Streptavidin assay plate could vary from 25-35 min.

Specificity

To determine the specificity of the assay for antibodies against rhASB, samples of anti-rhASB or anti-rhIDU were tested in naïve human serum. Anti-rhASB was prepared at 100, 1000, or 50,000 ng/mL, and anti-IDU was prepared at 50,000 ng/mL. Antibodies against rhIDU were chosen as a control since rhIDU also contained the mannose-6-phosphate post-translational modification that could potentially have specific binding to antibodies through epitopes that are not unique to rhASB. The signal for 50,000 ng/mL anti-IDU was below the signal for 100 ng/mL anti-rhASB, indicating the assay is highly specific for anti-rhASB antibodies.

Reagent Stability

To characterize the robustness of preparation and storage stability of the rhASB reagents, rhASB reagents were prepared in multiple lots and used to analyze equivalent samples of purified antibody into naïve human serum. Aliquots of three lots were stored at 4° C., −20° C., and −70° C. after an initial storage period of 7 weeks at 4° C. Over a two-month period, aliquots from different storage temperatures were used to analyze equivalent samples of purified antibody into naïve human serum. The robustness of reagent preparation was tested by making multiple small lots of reagent and testing them against the positive control dilution. Although variability was observed across the lots, the sensitivity was similar. Three lots were used to test the stability under storage conditions, which was maintained across an 8-week period at all three storage temperatures. In study validation has demonstrated reagent stability up to 6 months with longer time periods under continued investigation.

System Suitability

To evaluate the system noise for the Sector PR400 reader, plates were run with no solution (dark noise), 2× Read Buffer T, or MSD Free Tag. The three variations were tested on both uncoated plates and standard Streptavidin plates. The dark noise had standard deviations of 14 and 15, respectively. The read buffer had standard deviations of 18 and 14, respectively. The free tag had CVs of 1.2% on uncoated plates. These numbers were calculated from 96 replicates. The variability for the system in the absence of any assay components was acceptable and unlikely to contribute to variability in sample measurement.

Precision

Precision was determined for positive controls at 100, 1000, and 50,000 ng/mL in neat serum. Two analysts obtained similar signals from all three samples across a total of five separate days. Across the seventeen runs, the CV % for 50 μg/mL, 1 μg/mL, 100 ng/mL, and 0 ng/mL G192 were 19%, 10%, 10%, and 7%, respectively. Two analysts obtained similar titer values across a total of three separate days. Across the six runs, the titer values spanned no more than two adjacent dilution factors for each concentration.

Sample Stability

To evaluate the stability of antibody samples to different storage conditions, the controls were subjected to multiple freeze-thaw cycles, multiple days of storage at 4° C., and multiple days of storage at 4° C. for the 1:10 screening dilutions. For anti-rhASB, the sample stability was established over 5 freeze-thaw cycles and 3 days of storage at 4° C. for either neat serum or 1:10 dilutions of neat serum.

Example 2

Detection of Human α-Glucosidase-Specific Antibodies from Serum

The purpose of this assay development was to create a method to assess the immunogenicity of human α-glucosidase (rhGAA). Many of the assay improvements incorporated into the rhASB assay were tested for the rhGAA assay, although not all were successful and further optimization was required.

The antibodies used to develop the assay were three separate rabbit polyclonal antibodies (BP32, J8255, J8266), which were purified using a Protein G column followed by rhGAA affinity chromatography.

Sample dilutions and stocks of Ru-rhGAA and biotin-rhGAA were prepared in 2% Blocker A [2% bovine serum albumin (BSA) in phosphate buffered saline (PBS)]. Equal volumes of Ru-rhGAA, biotin-rhGAA, and sample dilutions were mixed in a preincubation plate. The preincubation plate was incubated at room temperature (RT) for 18-22 hours. The Streptavidin assay plate was blocked with 150 μL per well 5% Blocker A at 4° C. overnight. The block was shaken out of the assay plate and 50 μL of each mixture was transferred to the blocked Streptavidin assay plate. The assay plate was incubated 25-35 min at RT, washed 3× PBS-Tween, and 150 μL per well of Read Buffer T was added. The plate was read in the Sector PR 400.

For the screening assay, the reagents were first preincubated in a low-binding white 96-well plate, 30 μL 4 μg/mL Ru-rhGAA, 30 μL 4 μg/mL biotin-rhGAA and 30 μL 1:10 dilutions of controls and samples were added to each well. The preincubation plate was sealed with foil seal and incubated at room temperature on plate shaker overnight. The MSD streptavidin plate (assay plate) was blocked with 150 μL of 5% blocking buffer (5% BSA) (MSD Blocker A) at 4° C. overnight. The following day, the solution in the Streptavidin plate was discarded and 50 μL per well transferred from preincubation plates to the assay plate. The assay plate was sealed and incubated for 30 minutes at room temperature on plate shaker. The plate was then washed three times with wash buffer. 150 μL of 2× Read Buffer T (MesoScale Discovery) was added to each well and the assay plate read at the appropriate wavelength.

Labeling rhGAA with Biotin and Ru

RhGAA was labeled in a similar manner as described for rhASB in Example 1. Experiments demonstrated that a challenge ratio of about 4 for both biotin-rhGAA and Ru-rhGAA yielded a label ratio of about 3. Subsequent optimization could identify conditions that yield a label ratio of about 1-2 to provide a balance from requiring labels on rhGAA to obtain signal while minimally altering rhGAA to avoid masking epitopes.

Sensitivity

To determine the lowest analyte concentration in serum that can be detected in this assay, but not necessarily quantitated, purified antibodies were prepared at 250-10,000 ng/mL in naïve pooled serum. The signal from 1:10 dilutions of prepared concentrations were compared to the signal from the matched dilution of naïve pooled serum.

The limit of detection varied depending on the individual polyclonal antibody, with better than about 1 μg/mL detection for all three sources. The assay was capable of detecting at least as low as about 250 ng/mL rabbit polyclonal antibody BP32 in neat serum.

Interference by Matrix

To evaluate the effect of the matrix (rat serum) on the concentration-response relationship, affinity-purified polyclonal antibody was prepared at 100-10,000 ng/mL in 0, 5, 10, 25, 50, and 100% naïve pooled serum in 2% Blocker A. Signals from 1:10 sample dilutions were compared to the 1:10 dilution of samples in 0% serum. At serum concentrations up to 25%, the accuracy was maintained in the range of 67-119%.

Interference by Free Drug

In addition, the signal from 1:10 sample dilutions into 10 µg/mL rhGAA was compared to the signal from 1:10 sample dilutions into 2% Blocker A. Although the assay was tolerant of free drug, the presence of 10 µg/mL rhGAA in the sample diluent was able to serve as a confirmatory test for positive results. This would correspond to a 100 µg/mL serum concentration, which was unlikely to occur in actual patient samples since that is 20% of the concentration of the drug formulation.

Establishment of Assay Cutpoint

To determine the signal that will result in a positive assay result using naïve sera from multiple individuals (cutpoint), the average assay signal for multiple naïve individuals was calculated from three replicates and standard deviation was calculated from the individual averages. The cutpoint was set at a 95% confidence interval to provide a 5% false positive rate. The standard deviation was multiplied by 1.645, i.e., the t-factor for a one-tailed 95% confidence interval.

Cutpoint factors for human matrices were established by assaying at least 50 naïve human sera or human CSF. Cutpoint factors for animal matrices were established by assaying 20 naïve rat sera, rabbit sera, feline sera, or feline CSF. Three replicates were used for each serum sample to match the samples, which were also analyzed in triplicate. In all cases, the standard deviation between the average signals for the individual sera was very close to the system variability (SD=16), indicating that variations for individual sera are not a significant factor for the assay.

System Suitability

The rhGAA assay showed plate artifacts with a loss of signal across columns, which was due to the length of time between adding the read buffer and reading the plate. A feasible work around was to design a plate layout in which the variability was spread within samples rather than between samples.

Example 3

Assay for Lysosomal Enzyme Neutralizing Antibodies

To evaluate the presence of rhASB activity neutralizing antibodies, an activity assay that had previously been developed at BioMarin as a lot release assay for purified rhASB was modified. The activity of rhASB is measured by the release of a fluorescent molecule from a fluorogenic substrate at pH 5.6 and is a validated assay under serum free conditions. The assay uses a synthetic substrate, 4-methylumbelliferyl sulfate (4-MUS), which is cleaved into free sulfate and 4-methylumbelliferone (4-MU) by rhASB. The activity assay is inhibited by phosphate and sulfate, both of which are present at variable amounts in patient serum. To produce an assay to detect neutralizing antibodies, an antibody isolation pretreatment step was developed to remove phosphate and sulfate under conditions in which antibody binding and rhASB enzyme activity were both maintained.

Antibody Isolation Pretreatment Evaluation

To isolate the antibodies from the phosphate and sulfate, an affinity purification step with Protein A/G was selected. The Protein A/G resin method requires an acidic elution step, which needs to be brought back to pH 5.6 in order to subsequently measure rhASB activity. Before testing the resin, it was established that 20 mL of 0.1 M glycine, pH 2.70, could be adjusted to pH 5.6 with either 6.9 mL of 1 M Na acetate, pH 7.20, or 3.4 mL of 2 M Na acetate, pH 7.29. Tris buffers at various pH values and molar concentrations were also examined, but were very sensitive to small volume differences. The 1 M Na acetate buffer was selected because the pH was less sensitive to variations in Na acetate volume.

Multiple approaches to bind and elute antibodies to Protein A/G were investigated. The first was a magnetic bead approach, which although reproducible, did not have sufficient binding capacity for this assay. Next, UltraLink Immobilized Protein A/G resin was tested and showed good elution as long as the resin was washed with water between binding and elution steps. The amount of antibody eluted was linear for up to 100 µL serum per 100 µL resin, with drop-off at 200 µL serum. Binding capacity was calculated as 600 µg antibody/100 µL resin at 200 µL serum. In order to ensure that saturation was not reached, subsequent serum binding steps were performed with 200 µL of a 1:2 serum dilution incubated with 100 µL resin, which corresponds to 200 µL slurry. Halving all volumes also resulted in similar yields and was adopted for later experiments to minimize the required sample volume.

To simplify the protocol and increase throughput, a plate-based method with vacuum filtration was examined in addition to the standard centrifugation method using the UltraLink Immobilized Protein A/G resin. For this method, the centrifuge steps were replaced with vacuum filtration steps. The percent inhibition from samples made by spiking purified antibodies into three different human sera was consistent across multiple analysts and days.

For antibody purification in the final format, the Protein A/G resin was mixed and 100 µL slurry was added to a Multiscreen plate. The liquid was removed by vacuum and then washed 1×400 µL PBS, pH 7.4. The serum was diluted 1:2 into PBS, pH 7.4, and 100 µL of the 2-fold dilution was used to resuspend the resin. The mixture was allowed to incubate for 1 hr at RT and the serum removed by centrifugation or vacuum. The resin was then washed 1×400 µL PBS, pH 7.4, and 2×400 µL purified water. The antibody was eluted in 2×10 min with 200 µL 0.1 M glycine, pH 2.70. The eluate was neutralized to pH 5.6 by the addition of 1 M sodium acetate.

Evaluation of Enzymatic Activity

The use of the isolation step resulted in an altered buffer composition relative to the lot release assay and the effect of this altered buffer on the linearity of rhASB activity was evaluated. Ten µL of rhASB stock at 0-62.5 ng/mL was mixed with 40 µL of glycine/acetate buffer and then incubated with 4-MUS substrate for 20 minutes. The glycine/acetate buffer system did not affect the ability of the glycine/carbonate stop solution to halt the sulfatase activity, and the linearity and time robustness previously observed was maintained.

The robustness of the neutralization step was evaluated by intentionally varying the volume of 0.1 M glycine, pH 2.70, from 180-220 µL and the volume of 1 M Na acetate from 62-76 µL and evaluating the activity of 0-62.5 ng/mL rhASB. Perturbations of 10% buffer composition yielded rhASB activity measurements within 10% of the values obtained for rhASB in the optimized combination of 200 µL glycine and 69 µL glycine. This indicates that small variation in pipetting is not anticipated to cause significant errors in measuring enzyme activity.

To measure enzyme activity in the final format, purified antibody was mixed with rhASB enzyme at 62.5 ng/mL. Purified antibody (40 µL) in glycine/acetate was combined with 10 µL 62.5 ng/mL rhASB (0.05 M acetate, pH 5.60, 0.05% TWEEN-20). The mixture was incubated in black low-binding flat bottom plate (e.g., Greiner) at 37° C. for 1 hour to permit binding of antibodies to rhASB. Pre-warmed 5 mM 4-MUS substrate (e.g., Sigma) in activity assay buffer was added to each well and incubated at 37° C. for 20 minutes. The reaction was stopped by adding 150 μL per well of stop buffer (0.35 M glycine, 0.44 M carbonate). The plate was read using SPECTRAmax Gemini plate reader with SoftMax Pro software with excitation at 366 nm and emission at 446 nm, with cutoff at 435 nm.

Specificity

In order to test this assay for specificity, 12.5 ng/mL rhASB was pre-incubated with various anti-rhASB antibodies (G192, BP14, BP15, J3549, J3550) at 0-150 μg/mL in naïve serum, and anti-Aldurazyme (recombinant human iduronidase (IDU)) antibody (BP13) at 40 and 150 μg/mL in naïve serum. The level of rhASB activity with antibody relative to naïve serum and buffer was compared.

Four of the five affinity-purified polyclonal anti-rhASB antibodies were able to inhibit rhASB activity relative to naïve serum: BP14, BP15, J3549, and J3550. The response was proportional to the amount of antibody spiked into the naïve serum. In contrast, polyclonal anti-Aldurazyme antibody (BP13), polyclonal anti-rhASB (G192), and naïve serum did not significantly reduce rhASB activity.

The inability of one polyclonal anti-rhASB (G192) to affect rhASB activity and the different responses for multiple polyclonal antibodies at the same concentration indicated that the assay was suitable for detecting neutralizing antibodies and did not reflect total antibody concentration. BP14 (rabbit anti-rhASB) was selected as a control in assay validation and sample runs since the response was the highest of the purified antibodies, potentially indicating a higher proportion of monoclonal antibodies that inhibit enzyme activity.

Establishing Cutpoint

To determine the lowest signal that would be considered positive, 50 naïve sera were tested to establish confidence interval (CI). The naïve sera showed a fairly wide distribution with a negative bias. To be 90% certain that a reduction was statistically significant, a one-tailed t-test was used to set the cutpoint at 10% (average plus 1.282 times standard deviation (SD)). The 95% confidence interval was 15% (average plus 1.645 times SD). The 99% confidence interval was 25% (average plus 2.326 times SD). The 90% confidence interval was selected for sample analysis.

Sensitivity

Previous experiments had shown that affinity-purified BP15 IgG polyclonal antibody from rabbit serum was able to neutralize the enzymatic activity of rhASB. The signal from rhASB without antibody or interfering serum was considered 100%. The signal from rhASB incubated with 11.8 μg/mL BP15 dropped by 54%. Therefore, the assay was able to detect inhibition of rhASB in the altered buffer conditions.

A BP14 dilution series was prepared at 2.5, 5, 7.5, 10, 15, and 20 μg/mL in pooled naïve human serum and compared to the 95% confidence interval. BP14 at 7.5 μg/mL or greater was able to bind to rhASB and inhibit the activity of rhASB beyond the 95% CI. BP14 at 10 μg/mL or greater was able to inhibit rhASB beyond the 99% CI. Since only a fraction of the antibody population may be able to inhibit enzymatic activity, the LOD is more accurately recorded as less than or equal to about 7.5 μg/mL.

Interference by Free Drug

Prior pharmacokinetic analysis showed that in patients on 24 weeks of infusion therapy showed that the rhASB in the plasma ranged from less than 100 ng/mL in more than 50% of patients to not greater than 663 ng/mL in any patient at the 5 hour time point. To evaluate the effect of free drug, 10-150 μg/mL anti-rhASB was prepared in naïve serum containing 0-1000 ng/mL rhASB. If free rhASB in the serum samples is retained through the antibody purification step, then it could result in higher signal in the activity assay and mask any reduction due to antibodies. For each concentration of rhASB, relative accuracy was calculated against 0 ng/mL rhASB.

At 10 ng/mL rhASB, the relative accuracy was 82-109%, without a strong bias. At 100 ng/mL rhASB, the relative accuracy was 47-76%, indicating that at this concentration of rhASB, the amount of protein retained through the antibody purification step did interfere with neutralizing antibody detection. Since rhASB concentrations above 10 ng/mL are unlikely seven days post infusion, the antibody isolation step is sufficiently robust to free drug interference.

Interference by Matrix

To evaluate the effect of the matrix (e.g., serum) on the antibody-activity response relationship, the serum was prepared using the Protein A/G resin method and the activity of rhASB for this serum sample was compared with that of buffer alone. Because serum had already been demonstrated to interfere with the assay, the ability of the sample preparation step was evaluated to determine the effectiveness in removing the interference. Across three experiments, the naïve serum was within 10% of the buffer control showing that the antibody purification step effectively removes the serum interference from the activity assay.

The recovery of antibodies was evaluated by preparing samples at 25 μg/mL anti-rhASB in multiple individual naïve sera and running three separate aliquots of each sample. The within individual CV was 2-13% for reduction of enzyme activity and 3-17% for total protein recovery. The between individual CV was 11% for reduction of enzyme activity, indicating that the individual matrix is not anticipated to cause significant variability in evaluating the presence of neutralizing antibodies.

Precision

In order to determine the capacity of the assay to give similar activity reduction for antibodies in serum across multiple sample preparations, separate aliquots of antibody preparations were run through the Protein A/G purification step and compared across analysts and days. The assay showed good reproducibility with 5.6-23.4% CV, with higher CV observed closer to the limit of detection. The precision in sample analysis provides an indication of its reliability during normal usage.

Robustness

It was also necessary to determine the capacity of the assay to remain unaffected by small, but deliberate, variations in method parameters and provide an indication of its reliability during normal usage.

A comparison of the percent reduction due to quality controls using assay concentrations of rhASB and 4-MUS at 80%, 100%, and 120% of the optimized values indicated that linearity of the assay was unaffected by 20% variations in 4-MUS and rhASB concentrations. Change in rhASB concentration resulted in a corresponding increase or decrease in % activity as expected. Varying the 4-MUS concentration from 4 mM to 6 mM affected the results slightly, with values remaining within 10% of the value for 5 mM 4-MUS at the same rhASB concentration. Additionally, the prepared sample yielded similar results from 0-4 days after processing with Protein A/G resin. These results demonstrate the robustness of the assay and the ability to withstand minor changes in assay variables.

The two antibody incubation steps times ranged from 30-65 minutes for the incubation of serum, from 5-20 minutes for the glycine elution, and from 40-65 minutes for the pre-incubation of purified antibody with rhASB. Based on these results, windows of 60-70 min, 10-15 min, and 60-70 min, respectively, are recommended for the assay.

Several robustness ranges were established for this assay. The acceptable temperature range was 36-38° C. The incubation time was robust from 19-21 minutes. The reagent expiration dates were also found to be reliable as 1 month for activity assay buffer, 2 months for stop buffer, and 1 year for 4-MUS.

Sample Stability

To evaluate the stability of antibody samples to different storage conditions, the controls were subjected to multiple freeze-thaw cycles, multiple days of storage at 4° C., and multiple days of storage at 4° C. for antibody eluate. For anti-rhASB, the sample stability was established over 5 freeze-thaw cycles and 4 days of storage at 4° C. for neat serum. The storage of the antibody eluate had poor accuracy and is not recommended for assay implementation.

Example 4

Measurement of Anti-Enzyme Antibodies that Interfere with Enzyme/Receptor Binding In order for lysosomal enzyme (LE) therapy to be successful, the LE must be taken up into cells and targeted to the lysosome. The uptake mechanism is primarily through binding of mannose-6-phosphate residues on the LE to the Calcium Independent Mannose-6-Phosphate Receptor (CI-MPR). The binding to this receptor has been determined to be necessary and sufficient for uptake (Dintzis et al., *J Biol Chem* 269:12159-66 (1994)). Therefore, the use of an assay to evaluate the neutralization of CIMPR binding can be used as a surrogate for neutralization of receptor-mediated uptake.

To evaluate the presence of receptor-binding neutralizing antibodies, a plate-based sCIMPR binding assay that had previously been developed at BioMarin for characterization of purified rhASB was modified. The original assay used rhASB activity to quantify the amount of rhASB present. Since the purpose is to distinguish between the two potential modes of neutralization, i.e., activity and binding, enzyme activity is not the preferred detection method for the adaptation to a neutralizing antibody assay. To produce an assay to detect neutralizing antibodies, rhASB labeled with biotin was used.

Purification of sCIMPR

The soluble extracellular domain of the CIMPR (sCIMPR) was purified from fetal bovine serum using a phosphomannan affinity column followed by acidic size exclusion chromatography (Valenzano et al., *Analytical Biochemistry* 209:156-162 (1993)). The extracellular domain (molecular mass of 250 kDa) comprises approximately 90% of the intact CIMPR molecule (molecular mass 275 kDa).

Evaluation of Biotin-rhASB Detection

Biotin-rhASB was prepared as described in Example 1. To evaluate the ability of the biotin-rhASB detection to substitute for the enzyme activity, a series of samples were investigated with both detection methods. The samples included blocking buffer alone, naïve serum, and a dilution series of an anti-rhASB polyclonal antibody known to inhibit receptor binding (BP14 or BP15).

For the activity readout, receptor binding was evaluated using an activity assay was carried out using the receptor, the enzyme, and the enzyme substrate. Plates (96-well, black, flat-bottom) were coated with 4 μg/ml sCIMPR and incubated at 4° C. overnight. Plates were washed 2 times with 200 μL/well and incubated in blocking buffer for 1 hour at RT. Samples were pre-incubated 20 minutes with 2 nM rhASB or 2 nM biotin-rhASB at RT on a shaker. Plates were washed 2 times and diluted samples were added at 100 μL/well and incubated for 1 hour at RT. During this incubation, substrate (5 mM 4-MUS) was diluted 1:2 in blocking buffer and equilibrated in a water bath (37° C. for 30 minutes). Samples on the plates were discarded, the plates were washed 2 times and the diluted substrate added to the plates at 100 μL/well. Plates were incubated 20 minutes at 37° C., on a plate incubator. The reaction was stopped by adding 150 μL/well glycine/carbonate buffer. Plates were read at ex=366 nm em=446 nm.

For the biotin-rhASB readout, receptor binding was evaluated using an activity assay was carried out using the receptor, the labeled enzyme, and a Streptavidin-HRP conjugate. In the receptor binding assay, a 96-well flat-bottom plate (Nunc Maxisorp) was coated with 4 μg/mL sCIMPR, incubated overnight at 4° C., and washed twice. 200 μL blocking buffer was added and the plate incubated for 1 hr at RT (~25° C.). Antibody containing serum and biotinylated rhASB (2 nM) were pre-incubated for 30 min at RT (~25° C.). Blocking buffer was removed by washing twice and 100 μL/well of Ab/biotin-rhASB solution added to the wells and incubated at 37° C. or RT (with or without shaking) for 1 hr. The plate was washed twice and 100 μL/well Streptavidin-HRP at 1:5000 was added at 37° C. for 30 min. The plate was washed twice and 100 μL/well TMB substrate added and color developed for approximately 30 min. The reaction was stopped with 100 μL/well 2 N sulfuric acid and the absorbance read at 450 nm.

The presence of the biotin label did not interfere with the binding of rhASB to sCIMPR. Results from the activity readout were very similar for the labeled and unlabeled material, indicating that the biotin label does not interfere with binding of rhASB to sCIMPR.

The correlation between the activity readout and the SA-HRP readout was investigated for biotin-rhASB. The signal generated from the binding of biotinylated rhASB to immobilized sCIMPR was considered 100%. Results of the receptor binding assay and the activity assay were similar for biotin-rhASB, demonstrating comparability between the activity based binding assay and the ELISA method. In addition, BP14 and BP15 antisera neutralized the interaction between rhASB and sCIMPR to similar levels relative to control for both assays. Since both BP14 and BP15 also inhibited enzyme activity, small differences in the two readouts were tolerable. Pre-bleed sera did not affect either assay readout.

Establishing Cutpoint

To determine the lowest signal that would be considered positive, 50 naïve sera were tested to establish a 95% confidence interval (CI) for signal reduction relative to pooled naïve serum. To be 95% certain that a reduction was statistically significant, a one-tailed t-test was used to set the cutpoint at 8.5% (1.645 times standard deviation (SD)). The 99% confidence interval was also calculated at 11.5% (2.326 times SD).

Specificity

Specificity of the assay was assessed using anti-rhIDU (BP13) incubated in the same manner as the sample serum. Anti-rhIDU did not significantly alter rhASB-sCIMPR binding at the same dilutions of antisera or at up to 125 µg/mL spiked into naïve sera.

Limit of Detection

To establish the lowest dilution of antibody that can neutralize rhASB/sCIMPR binding more than the cutpoint, purified G192 was spiked into naïve human serum in a dilution series at 15, 20, 25, 30, 35, 40, 45, and 50 µg/mL. Although 35 µg/mL was able to reduce binding more than the cutpoint of 8.5%, the variability was very high. The lowest concentration that was able to reduce binding with acceptable precision was 45 µg/mL. Since only a fraction of the antibody population may be able to inhibit enzymatic activity, the LOD is more accurately recorded as less than or equal to about 45 µg/mL.

Although the LOD is high, the inhibition of rhASB binding to sCIMPR is anticipated to require multiple antibody interactions as each rhASB molecule contains multiple mannose-6-phosphate glycosylation sites that can mediate receptor binding. Due to this requirement, higher concentrations of multiple antibodies capable of blocking binding through a single mannose-6-phosphate residue may be required to have a functional effect.

Low concentrations of antibody resulted in a negative percent reduction that was statistically significant from the 50 naïve individuals. This enhancement of receptor binding in vitro may indicate that some antibody clones may actually enhance rhASB binding to CIMPR in vivo. For the purposes of identifying neutralizing antibodies, any negative percent reduction samples are considered to be below the LOD for the assay.

Interference by Free Drug

Prior pharmacokinetic analysis showed that in patients on 24 weeks of infusion therapy showed that the rhASB in the plasma ranged from less than 100 ng/mL in more than 50% of patients to not greater than 663 ng/mL in any patient at the 5 hour time point. Free rhASB in the serum samples could inhibit the binding of biotin-rhASB by competing for binding sites on sCIMPR. To examine the ability of free rhASB to decrease antibody-mediated inhibition of binding, increasing amounts of rhASB (10, 50, and 100 ng/mL) were incubated with low (10 µg/mL), intermediate (50 µg/mL), and high (100 µg/mL) concentrations of BP14 in 10% serum, and compared to binding in standard conditions. For each concentration of rhASB, relative accuracy was calculate against 0 ng/mL rhASB.

When rhASB levels were greater than 10 ng/mL, the concentration response relationship failed to meet acceptance criteria of accuracy between the samples with and without interfering free drug within 75-125%. Therefore, the level of free drug must remain less than or equal to 10 ng/mL in order for the assay to be accurate. Since rhASB concentrations above 10 ng/mL are unlikely seven days post infusion, the assay is sufficiently robust to free drug interference.

Interference by Matrix

To evaluate the effect of the matrix (e.g., serum) on the concentration-response relationship, 10-100 µg/mL anti-rhASB antibody was diluted in 0-20% human serum. Results demonstrated that 20% serum decreased the measured neutralization of rhASB-sCIMPR binding by 50% or more. At 10% serum, the signal was decreased by 2.5-12% relative to 0% serum. Therefore, the recommended minimum dilution factor is 10.

Precision

A set of quality controls at 43, 72, and 125 µg/mL anti-rhASB were evaluated by two analysts over multiple days. The intra-assay precision was evaluated between replicates on a single plate and generated CV 1-15%. The inter-assay precision was evaluated as the coefficient of variation across all replicates, and was 5-7% across six separate plates.

Robustness

Small deviations in assay parameters, including incubation temperature and concentration of biotin-rhASB, were examined to determine the effect on assay performance. Small deviations in method parameters must not result in assay changes exceeding 20%, except at the LOD where assay changes must not exceed 25%.

Incubation times from 50-70 minutes for serum and rhASB-biotin, 50-70 minutes for serum/rhASB-biotin with sCIMPR, and 20-40 minutes for SA-HRP were evaluated using 43, 72, and 125 µg/mL anti-rhASB and determining relative accuracy to the standard conditions. The 43 µg/mL sample was very sensitive to changes in incubation times, so the recommendation for incubation times is for narrower windows of 10 minutes total.

Sample Stability

To evaluate the stability of antibody samples to different storage conditions, the controls were subjected to multiple freeze-thaw cycles. For anti-rhASB, the sample stability was established over 3 freeze-thaw cycles.

Example 5

Measurement of IgE Isotype Anti-rhASB Antibodies

A reversed immunoassay (anti-rhASB IgE ELISA) was developed for use in detecting the presence of rhASB-specific IgE antibodies in human serum, relative to the range of responses exhibited by serum samples from a naïve human population. The assay involves the binding of anti-human IgE antibody to an ELISA multiwell plate, binding of a serum sample to the IgE antibody, and detection by biotinylated rhASB and Streptavidin-HRP conjugate.

Cutpoint

To identify the lowest concentration of analyte that can be detected, but not necessarily quantified, in the assay control ranges of baseline IgE background were established by testing a panel of naïve human serum (50 samples). The signal distribution for individual naïve sera was determined for 50 human serum samples. The difference relative to a pooled lot was calculated on each assay plate. The average and standard deviation was calculated from the individual signals. The 95% confidence interval was calculated as 0.030 (1.645×SD). The 95% confidence interval was used as a cutpoint factor, which was then added to the average from the naïve serum pool on each assay plate to obtain the plate cutpoint. The use of a 95% CI will lead to approximately a 5% false positive rate (95% Confidence Interval). Amobg the 50 naïve human serum samples tested, 3 had absorbance values higher than the cutpoint, yielding a 6% false positive rate.

Limit of Detection

The LOD was the analyte concentration for which the measured mean response is more than the average from the pooled naïve human serum plus the cutpoint factor. Since a human IgE anti-rhASB was not available, the limit of detection was estimated using 0.41-300 ng/mL rabbit IgG anti-rhASB and an alternate capture antibody. Concentrations at or below 0.41 ng/mL were below the plate cutpoint. Therefore, about 1.23 ng/mL can be considered the LOD for this assay.

Selectivity and Specificity

To test the specificity of anti-rhASB IgE detection, several parameters were examined during the validation. To confirm that signal was due to rhASB-specific antibodies, unlabeled rhASB was added during the incubation with biotin-rhASB to demonstrate the rhASB-specific competition for rabbit IgG anti-rhASB. With the addition of 2000 ng/mL, 64.6% and 52.1% inhibition were observed for the 20 and 50 ng/mL anti-rhASB controls, respectively. Additionally, 50 ng/mL rabbit anti-rhIDU antibody gave a signal significantly below the LOD with an absorbance virtually equal to the buffer background level. These results indicated that the assay was specific for rhASB antibodies.

Interference from Free Drug

Since IgE samples could potentially be collected immediately after a hypersensitivity reaction, there is the possibility that significant levels of rhASB may be present from the infusion.

To evaluate the effect of free drug on the concentration response relationship, a combination of increasing unlabeled rhASB and anti-rhASB IgG was tested. RhASB (2, 20 and 200 ng/mL) and anti-rhASB (2, 5, 20 and 100 ng/mL) were used, and the effect of free drug and the accuracy of the antibody were determined. Mixtures were prepared in cluster tubes and incubated for 1 hour at RT with gentle shaking before loading onto the assay plate.

Different levels of inhibition upon addition of rhASB to rabbit anti-rASB IgG in the assay were observed. This inhibition, reflected by the reduction of percent accuracy, correlated to the rhASB concentration added and to the rabbit anti-rhASB IgG concentration. In the presence of 2 ng/mL rhASB (100 ng/mL serum level after adjusting with a dilution factor of 50), the accuracy between the samples with and without the interfering free drug was 83.2-98.0%. The accuracy fell beyond the 80-120% acceptable range with 20 or 200 ng/mL rhASB present. At all three levels of rhASB tested, the accuracy percentage fell lower with increasing level of anti-rhASB IgG concentration, suggesting that the inhibition of rhASB to this assay format is mostly due to rhASB bound to the anti-rhASB antibodies in the serum samples.

Interference from Matrix

To evaluate the effect of serum on the concentration-response relationship, the effect of 1%, 2%, and 10% human serum on the accuracy of the rabbit IgG anti-rhASB standards was assessed.

Within the linear range of the curve (1.2 ng/mL to 100 ng/mL), the accuracy between the samples with increasing amounts of interfering serum (1%, 2%, and 10%) was within 80-103%. Two percent serum matrix provided the widest linear range with acceptable accuracy, so the recommended dilution factor during the sample analysis is 50.

Interference from IgG

To identify an appropriate capture antibody, curves of human IgG and human IgE were coated on a plate and detected with various anti-human IgE directly labeled with either biotin or HRP. The antibody selected for assay development had a lower signal for 300 ng/mL IgG than for 0.41 ng/mL IgE. This about 730-fold difference will ensure that total IgE is preferentially captured over total IgG. Some IgG may be captured, but the IgG antibodies that will specifically bind the detectable rhASB will only be a fraction of that inadvertently captured IgG.

To evaluate the interference from other antibody isotypes, the anti-human IgE coat was incubated with IgE standards, IgG standards, or samples containing equimolar concentrations of IgE and IgG. The presence of IgG did not interfere with the measurement of IgE in a total IgE format. Also, the IgG standards did not produce any signals significantly above the buffer background level, as were observed with the IgE standards.

To determine if the assay was specific to IgE, and the concentration-response relationship for IgE was not significantly affected by IgG present in the samples, an equal amount of IgG was added to IgE standards. This parameter was tested in the anti-human IgE coating format. A calibration curve of human IgE ranging from 0.07 to 50 ng/mL was prepared with and without human IgG, and analyzed in the total human IgE format. Within the linear range of the total IgE curve (0.21 ng/mL to 16.7 ng/mL), the accuracy between the samples with and without the interfering anti-rhASB IgG was within 88.4-106.5%, showing no interference from IgG.

Precision

The intra- and inter-assay precisions were examined by testing low (0.4 ng/mL), intermediate (3 ng/mL), and high (20 ng/mL) concentrations of rabbit IgG anti-rhASB. The intra-assay precision was calculated as the CV % from the triplicate samples and was within 1-5% across six plates. The inter-assay precision was calculated as the CV % for the average values for the six plates and was within 2-11%, with higher CV % for lower concentrations.

Robustness

Robustness assays indicate the assay can accurately measure up to 10% changes in standard concentration and the effect of multiple freeze thaw of samples does not affect the assay outcome.

Small variations in assay parameters, including incubation temperature and concentration of detection reagents, were examined to determine the effect of assay performance. Incubation times were examined at 90, 100, and 110% of the optimized times (10 min for TMB development, 60 min for all other steps) and concentrations were examined at 90, 100, and 110% of the established concentrations. To evaluate the effect on assay performance, 0.07-16.7 ng/mL rabbit IgG anti-rhASB were tested and accuracy of back calculation to a standard curve was determined. For all conditions tested, accuracy was within 85-110% for values above the limit of detection.

Sample Stability

To evaluate the stability of antibody samples to different storage conditions, samples were subjected to multiple freeze-thaw cycles. For rabbit IgG anti-rhASB, the sample stability was established over 3 freeze-thaw cycles.

Numerous modifications and variations in the invention as set forth in the above illustrative examples are expected to occur to those skilled in the art. Consequently only such limitations as appear in the appended claims should be placed on the invention.

What is claimed:

1. A method for detecting lysosomal enzyme (LE)-specific antibodies in a human comprising the steps of:
   (a) contacting a body fluid sample from the human with a first lysosomal enzyme labeled with a capture moiety and a second lysosomal enzyme labeled with a detection moiety to form a LE-specific antibody/lysosomal enzyme complex,
   (b) capturing the LE-specific antibody/lysosomal enzyme from step (a) by contacting the LE-specific antibody/ lysosomal enzyme complex with a solid support that specifically binds to the capture moiety, and (c) detecting the presence of captured LE-specific antibody from the body fluid sample by detecting the presence of the second lysosomal enzyme labeled with the detection moiety.

2. The method of claim 1, wherein the capture moiety of the first lysosomal enzyme is bound to the solid support via non-covalent interaction.

3. The method of claim 2, wherein the non-covalent interaction is biotin-avidin interaction.

4. The method of claim 1, wherein the body fluid, first lysosomal enzyme and second lysosomal enzyme are all contacted together in the same solution.

5. The method of claim 1, wherein the body fluid, first lysosomal enzyme and second lysosomal enzyme are contacted together for at least about 30 minutes prior to step (b).

6. The method of claim 1, wherein the molar concentration of the first lysosomal enzyme is about the same or less than the molar concentration of the second lysosomal enzyme.

7. The method of claim 1, wherein the first lysosomal enzyme and the second lysosomal enzyme are used in about equimolar ratios.

8. The method of claim 1, wherein the limit of detection is less than about 500 ng/mL.

9. The method of claim 1, wherein the limit of detection is less than about 100 ng/mL.

10. The method of claim 1, wherein the limit of detection is about 1.7 ng/mL to about 8.5 ng/mL.

11. The method of claim 1, wherein LE-specific antibodies can be detected from a species selected from the group consisting of human, cynomolgus monkey, feline, canine, rabbit, rat and mouse.

12. The method of claim 11, wherein the species is human.

13. The method of claim 1, wherein the body fluid is serum.

14. The method of claim 1, wherein the first and second lysosomal enzyme are recombinant human arylsulfatase (rhASB).

15. The method of claim 1, wherein the first and second lysosomal enzyme are recombinant human α-glucosidase (rhGAA).

16. A method for detecting lysosomal enzyme (LE)-specific antibodies in a human comprising the steps of:

(a) capturing the LE-specific antibody in a body fluid sample from the human by contacting the body fluid sample with a first lysosomal enzyme bound to a solid support, (b) contacting captured LE-specific antibody from step (a) with a second lysosomal enzyme labeled with a detection moiety, and (c) detecting the presence of captured LE-specific antibody from the serum sample by detecting the presence of the second lysosomal enzyme labeled with the detection moiety.

\* \* \* \* \*